US00PP22609P2

(12) United States Plant Patent
Blom

(10) Patent No.: US PP22,609 P2
(45) Date of Patent: Mar. 27, 2012

(54) ***CHRYSANTHEMUM* PLANT NAMED 'ZANMUBLAST'**

(50) Latin Name: ***Chrysanthemum×morifolium* Ramat.**
Varietal Denomination: Zanmublast

(75) Inventor: Wilhelmus Bernardus Blom, Leimuiden (NL)

(73) Assignee: Chrysanthemum Breeders Association B.V., Valkenburg Z-H (NL)

( * ) Notice: Subject to any disclaimer, the term of this patent is extended or adjusted under 35 U.S.C. 154(b) by 0 days.

(21) Appl. No.: 12/926,545

(22) Filed: Nov. 24, 2010

(51) Int. Cl.
*A01H 5/00* (2006.01)

(52) U.S. Cl. ..... Plt./296

(58) Field of Classification Search ..... Plt./296
See application file for complete search history.

*Primary Examiner* — Annette Para

(74) *Attorney, Agent, or Firm* — Steptoe & Johnson LLP

(57) ABSTRACT

A *chrysanthemum* plant named 'Zanmublast' characterized by its medium sized blooms with orange ray florets and prolific branching; natural season flower date October 5; blooming for a period of 4 weeks.

3 Drawing Sheets

Botanical designation: *Chrysanthemum×morifolium* Ramat.

Cultivar denomination: 'Zanmublast'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmublast'. 'Zanmublast' is a product of a breeding and selection program for outdoor pot mums (garden mums) which had the objective of creating new cultivars with a double type inflorescence, a natural season flowering date around October 5, blooming for a period of 4 weeks. 'Zanmublast' is a seedling resulting from a cross of the female parent id 9376 with the male parent id 17772. Plants of the new cultivar 'Zanmublast' differ from plants of the female parent in plant vigor. The plants of the seedling are more vigorous than those of the female parent. Plants of the new cultivar 'Zanmublast' differ from plants of the male parent in plant shape. The plants of the seedling are more ball-shaped than those of the male parent.

The new and distinct cultivar was discovered and selected as a flowering plant by Wilhelmus Bernardus Blom on a cultivated field in Rijsenhout, The Netherlands in 2005. The first act of asexual production of 'Zanmublast' was accomplished when vegetative cuttings from the initial selection in 2005 were propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
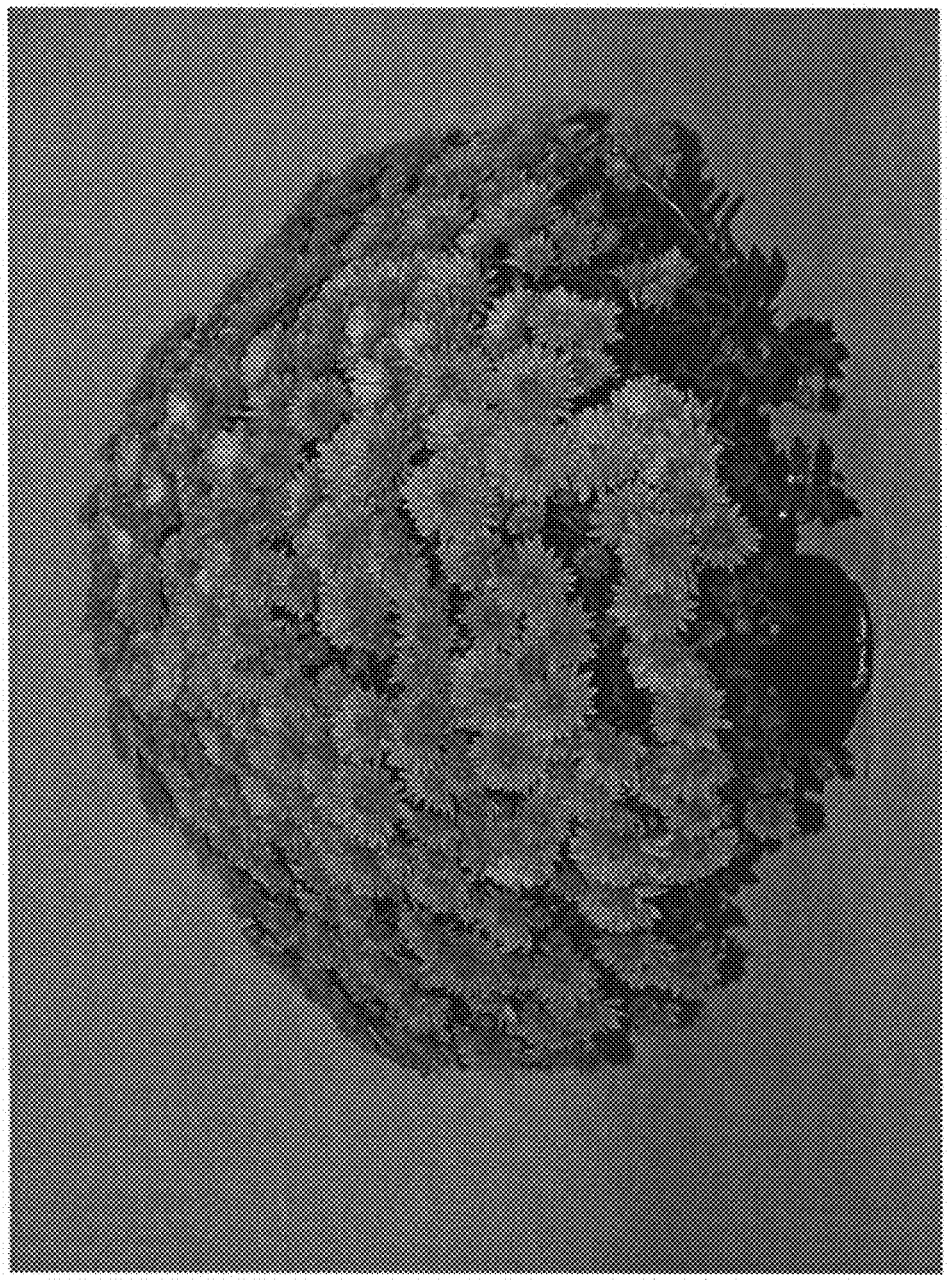
FIG. 1 shows a plant of the cultivar in full bloom.
Figure 2:
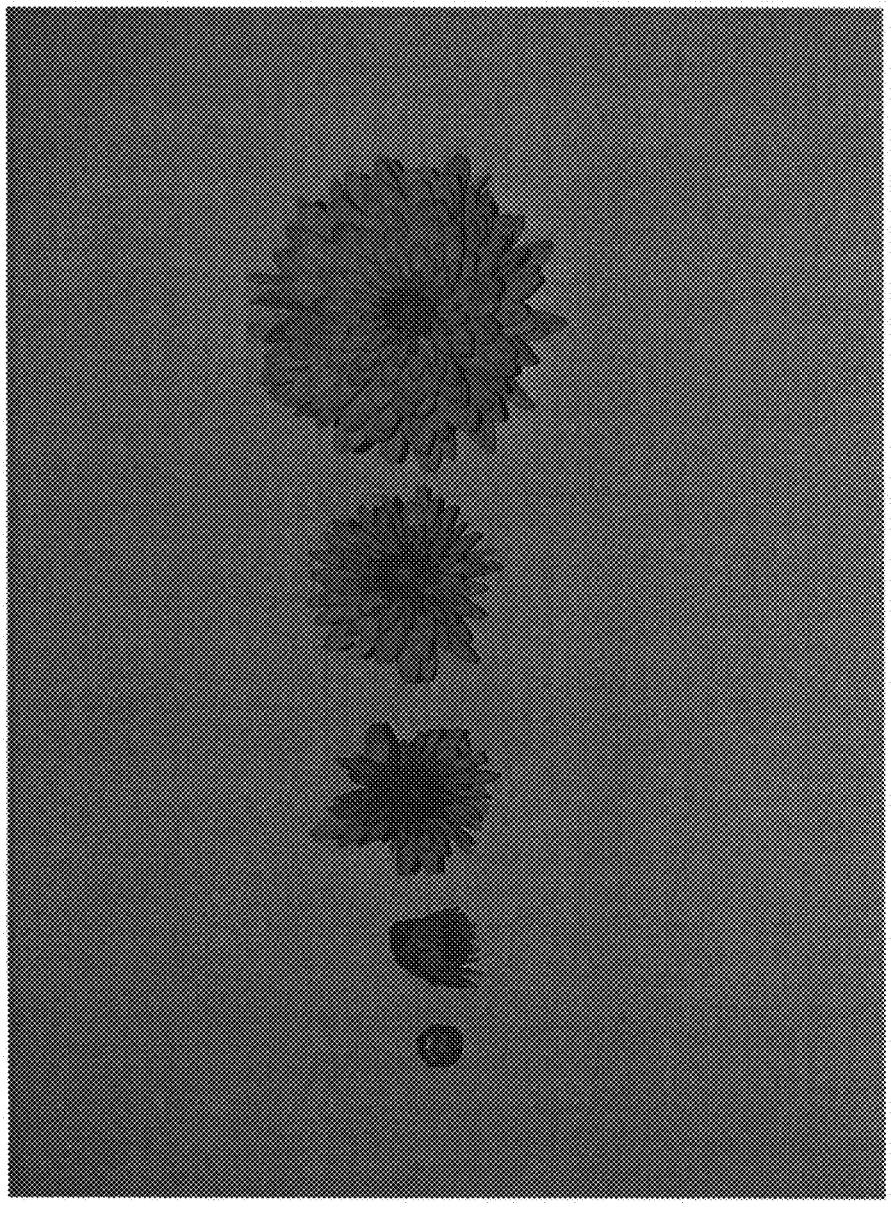
FIG. 2 shows the various stages of bloom of the new cultivar.
Figure 3:
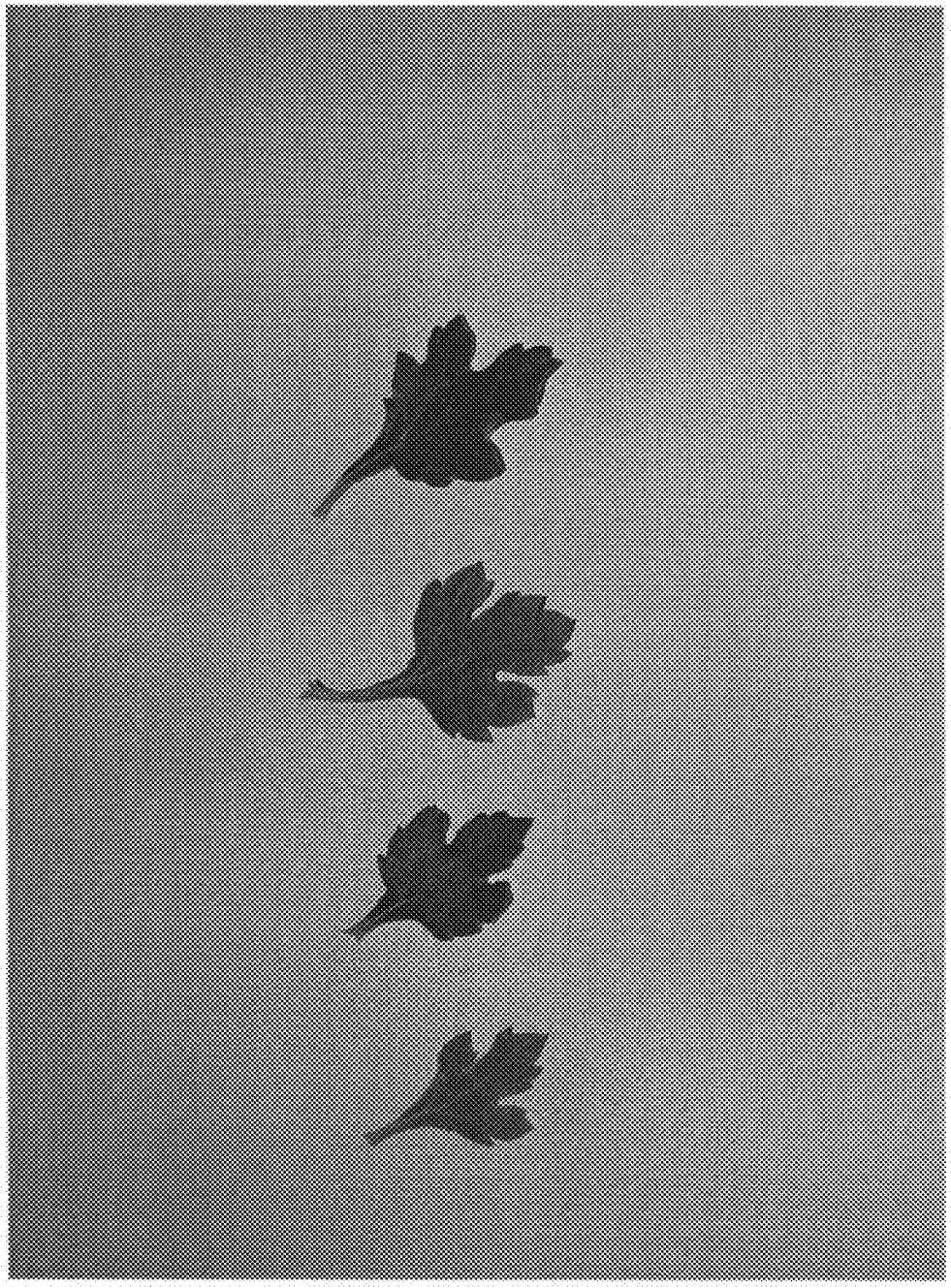
FIG. 3 shows the various stages of foliage of the new cultivar.

The observations and measurements were gathered from plants grown out door in Rijsenhout, The Netherlands under natural day length and temperature and planted in week 23 in 2009. The natural blooming date of this crop was October 5. The average height of the plants was 30 cm. No growth retardants were used. No tests were done on disease or insect resistance or susceptibility. No tests were done on cold or drought tolerance. This new variety produces medium sized blooms with orange ray florets blooming for a period of 4 weeks.

From the cultivars known to inventor the most similar existing cultivar in comparison to 'Zanmublast' is 'Zanmufay' (U.S. patent application Ser. No. 12/591,868). When 'Zanmufay' and 'Zanmublast' are being compared the following differences are noticed. (1) Natural season flowering date. And (2) Plant vigor. (1) Plants of 'Zanmublast' flower earlier than those of 'Zanmufay'. (2) Plants of 'Zanmublast' are more vigorous than those of 'Zanmufay'.

The following is a description of the plant and characteristics that distinguish 'Zanmublast' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, edition 2001.

TABLE 1

Botanical Description of *Chrysanthemum xmorifolium* Ramat. 'Zanmublast'

| Bud | |
|---|---|
| Size | Small; cross-section 5 mm, height 5 mm |
| Shape | Round |
| Texture | Pubescent |
| Outside Color | Greyed-green 191A |

TABLE 1-continued

Botanical Description of *Chrysanthemum xmorifolium* Ramat. 'Zanmublast'

| | |
|---|---|
| Phyllaries | |
| Number | 22-24, arranged in 3 rows |
| Shape | Elliptic |
| Apex | Acute |
| Base | Truncate |
| Margin | Entire |
| Color | Upper surface: Greyed-green 191B |
| Length and width | 5 mm; 2 mm |
| Texture | Pubescent |
| Inflorescence | |
| Type | Double |
| Height | 1 cm |
| Diameter | 5.5 cm |
| Peduncle length | 6.5-8 cm |
| Peduncle color | Green 138B-C |
| Peduncle diameter | 1.8 mm |
| Peduncle texture | Pubescent |
| Number per branch | Approx 8-10 inflorescences |
| Duration of flowering | 4 weeks |
| Seeds | Produced in small quantities, ovate, Greyed-brown 199A, length 1.5 mm, diameter 0.5 mm |
| Fragrance | Faint *chrysanthemum* odor |
| Color | |
| Center of inflorescence (disc florets) | Immature stage: Yellow-green N144D<br>Mature stage: Yellow 7A |
| Color of upper surface of the ray-florets | Greyed Orange 163D at base, Yellow-orange 22B at upper part |
| Color of the lower surface of the ray-florets | Greyed-orange 163 C |
| Tonality from Distance | A garden *mum* with orange flowers |
| Color of the ray-florets after aging of the plant | Greyed-orange 163B |
| Ray florets | |
| Texture | Upper and lower surface smooth |
| Number | Ca 180 |
| Shape | Elliptic |
| Apex | Dentate |
| Base | Attenuate |
| Cross-section | Flat |
| Longitudinal axis of majority | Straight |
| Length of corolla tube | 2-4 mm |
| Ray-floret margin | Entire |
| Ray-floret length | 1.5-2.5 cm |
| Ray-floret width | 4-5 mm |
| Ratio length/width | High |
| Disc florets | |
| Disc diameter | 2-4 mm |
| Number of disc florets | Ca. 15 |
| Shape | Tubular |
| Color | Yellow-green 145C at base to Green Yellow 1D at top |
| Length | 4 mm |
| Receptacle | |
| Color | Yellow-green 145D |
| Shape | Domed raised |
| Height | 5 mm |
| Diameter | 5 mm |
| Reproductive Organs | |
| Androecium | Present on only disc florets |
| Stamen length | 3 mm |
| Stamen color | Yellow-green 144A |

TABLE 1-continued

Botanical Description of *Chrysanthemum xmorifolium* Ramat. 'Zanmublast'

| | |
|---|---|
| Anther color | Yellow 6D |
| Pollen | Present in small amount |
| Pollen color | Yellow 13A |
| Gynoecium | Present on both ray and disc florets |
| Style color | Yellow-green 154C |
| Style Length | 3 mm |
| Stigma color | Yellow 7A |
| Stigma Width | 1 mm |
| Ovary | Enclosed in calyx |
| Plant | |
| Form | Grown as a spray type pot *mum*, outdoor raised and mounded |
| Growth habit | Spherical shape |
| Growth rate | High |
| Height | 30 cm |
| Width | 50 cm |
| Stem Color | Greyed-brown 199A |
| Stem Strength | Strong |
| Stem Brittleness | Not brittle |
| Stem Anthocyanin Coloration | Not observed |
| Internode length | 1-2.5 cm |
| Length of lateral branch | From top to bottom 20 cm |
| Lateral branch color | Green 137 C |
| Lateral branch, attachment | Strong |
| Lateral branch diameter | 2 mm |
| Branching (average number of lateral branches) | Prolific with 7 breaks after pinching |
| Natural season blooming date | October 5 (week 41) |
| Foliage | |
| Leaf color | Upper side: Green 139A<br>Lower side: Green 139c |
| Color midvein | Upper side: Yellow-green 147D<br>Lower side: Yellow-green 148D |
| Size | Small; length 4-5 cm, width 2-2.8 cm |
| Quantity (number per lateral branch) | Ca.26 |
| Shape | Elliptic |
| Texture upper side | Sparsely pubescent |
| Texture under side | Pubescent |
| Venation arrangement | Palmate |
| Shape of the margin | Serrated |
| Shape of Base of Sinus Between Lateral Lobes | Rounded |
| Margin of Sinus Between Lateral Lobes | Diverging |
| Shape of Base | Attenuate to truncate |
| Apex | Mucronulate |
| Petiole length | 1-2 cm |
| Petiole diameter | 2 mm |
| Petiole color | Yellow-green 147D |

TABLE 2

Differences with the comparison variety (when grown side to side)

| | 'Zanmublast' | 'Zanmufay' |
|---|---|---|
| Natural season flowering date | week 41-45 | week 42-46 |
| Plant width | 50 cm | 45 cm |

I claim:

1. A new and distinct *chrysanthemum* plant named 'Zanmublast' as described and illustrated.

* * * * *